(12) United States Patent
Cheetham

(10) Patent No.: US 8,690,570 B2
(45) Date of Patent: Apr. 8, 2014

(54) MIXING AND DISPENSING CONTAINER

(75) Inventor: Joshua James Cheetham, Bensenville, IL (US)

(73) Assignee: SDI North America Inc., Bensenville, IL (US)

( * ) Notice: Subject to any disclaimer, the term of this patent is extended or adjusted under 35 U.S.C. 154(b) by 0 days.

(21) Appl. No.: 13/242,017

(22) Filed: Sep. 23, 2011

(65) Prior Publication Data

US 2012/0295221 A1  Nov. 22, 2012

(30) Foreign Application Priority Data

Sep. 24, 2010  (AU) ................................ 2010904327

(51) Int. Cl.
*A61C 5/04* (2006.01)

(52) U.S. Cl.
USPC .............................................. 433/90; 433/89

(58) Field of Classification Search
USPC ............ 433/80–82, 89–90; 206/219, 22, 568, 206/221, 220, 63.5, 222, 368; 222/129, 222/136, 541.3, 541.4, 145.1, 145.5, 541.1, 222/386, 326–327
See application file for complete search history.

(56) References Cited

U.S. PATENT DOCUMENTS

| 4,941,751 | A | * | 7/1990 | Muhlbauer | 366/182.1 |
| 6,869,284 | B2 | * | 3/2005 | Aoyagi et al. | 433/90 |
| 2001/0053511 | A1 | * | 12/2001 | Aoyagi et al. | 433/90 |
| 2004/0011815 | A1 | * | 1/2004 | Martin | 222/136 |
| 2004/0020796 | A1 | * | 2/2004 | Cheetham et al. | 206/63.5 |
| 2006/0083632 | A1 | * | 4/2006 | Hammond et al. | 417/375 |

* cited by examiner

*Primary Examiner* — Yogesh Patel
(74) *Attorney, Agent, or Firm* — William H. Holt

(57) ABSTRACT

A container (10) for mixing and dispensing material comprising a body (12) having a main chamber (17), a dispensing nozzle (26), a liquid receptacle (14) and a plunger (18). The liquid receptacle (14) has a side wall (37) and a front wall portion (36) which is caused to break away from the side wall under pressure being applied by a plunger (18) so that the plunger and front wall portion can traverse the entire length of the body (12). This enables a charge of material in the main chamber (17) to be dispensed through a frangible wall or membrane (22) into the nozzle (26). The container 10 has a compression zone with a stepped region (50) for providing limited resistance to movement of the plunger and broken away end wall for use with low viscosity material for reducing the risk of uncontrolled extrusion of low viscosity material.

5 Claims, 3 Drawing Sheets

MIXING AND DISPENSING CONTAINER

FIELD OF THE INVENTION

The present invention relates to a mixing and dispensing container.

SUMMARY OF THE INVENTION

In accordance with one aspect of the present invention there is provided a dental container for mixing and dispensing of components of a dental mixture, having a main chamber, a dispensing nozzle, a liquid receptacle and a plunger, wherein the container comprises a body having a proximal end and a distal end, the main chamber being located adjacent the distal end of the body, the main chamber having a distal wall which is frangible and forms a seal and the dispensing nozzle being mounted at the distal end of the main chamber, the liquid receptacle being mounted within the proximal end of the body, and the plunger being sealingly mounted within an interior of the liquid receptacle, the liquid receptacle having an inner transverse wall which contains a weakened portion and wherein the plunger has a front face which is projection free, the liquid receptacle containing a liquid and the main chamber containing a powder, the arrangement being such that, in use, pressure is applied to the plunger to build up hydraulic pressure by means of the liquid on the inner transverse wall so as to break the weakened portion hydraulically and cause the liquid to enter the main chamber, and wherein a front portion of the liquid receptacle is arranged to be broken away from the remainder of the liquid receptacle by further depression of the plunger such that the plunger and the broken away portion of the liquid receptacle are able to traverse the entire length of the main chamber to cause dispensation of mixed dental material into the dispensing nozzle by application of hydraulic pressure on the distal wall of the main chamber so as to rupture the distal wall, and wherein the main chamber has a compression zone to impart resistance to movement of the broken away portion of the liquid receptacle.

DESCRIPTION OF THE DRAWINGS

The present invention will now be described, by way of example, with reference to the accompanying drawings, in which.

DETAILED DESCRIPTION OF THE DRAWINGS

Referring to the FIGS. 1 to 5, there is shown a container that is particularly envisaged to be used for dispensing of a dental material, in which a front part of a liquid receptacle breaks away from the liquid receptacle.

Figure 1:
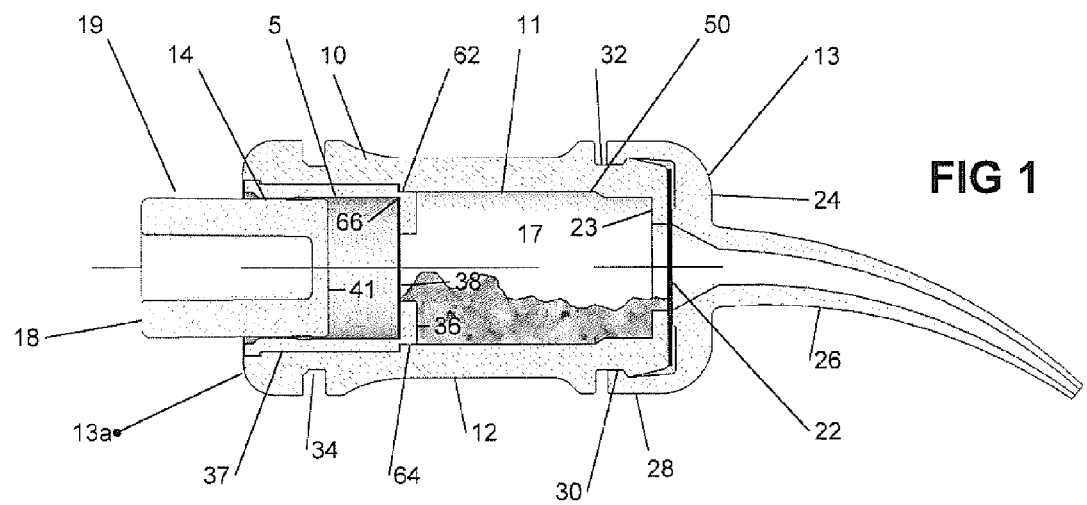
FIG. 1 is a longitudinal sectional view of a container in accordance with the present invention in an initial condition.

Referring to FIG. 1, there is shown a container 10 in an initial open or storage condition. The dental container 10 comprises a body 12 which has an internal surface 11 and is substantially cylindrical in cross section. Inside the body 12 is an open ended liquid receptacle 14, which, in use, contains a liquid (not shown). The receptacle 14 is sealed by a plunger 18 such as by seal means located on an external surface 19 of the plunger 18 or on an internal surface 15 of the liquid receptacle 14. The plunger 18 is located in an open end of the receptacle 14 as shown and has a front face 41.

The body 12 contains a main chamber 17 which is arranged, in use, to house an amount of powder (not shown). The body 12 is sealed at a distal end 13 by a frangible membrane 22 which is connected to the body 12 such as at an annular inwardly extending flange 23 by any convenient means such as an adhesive. The distal end 13 of the body 12 is opposed to a proximal end 13a thereof. The body 12 has attached thereto an end cap 24 which is connected to a nozzle 26 for dispensing material. The cap 24 is connected to the body 12 by means of a circumferential flange 28 which has an inwardly extending annular rib 30 at an end thereof remote from the nozzle 26. The rib 30 engages with a circumferential recess 32 in the body 12.

There is preferably provided a liquid tight seal (not shown) between the receptacle 14 and of the plunger 18. The seal may comprise annular ribs which extend outwardly from the receptacle 14 to the plunger 18 or vice versa.

Further, the body 12 is provided with an outward facing circumferential groove 34 adjacent the plunger 18. The groove 34 is arranged to engage with a dispensing apparatus (not shown) in use.

Still further, the liquid receptacle 14 has a side wall 37 and an inner wall 36 with a central weakened portion 38. The central weakened portion 38 is substantially thinner than the remainder of the inner wall 36 of the liquid receptacle 14. The inner wall 36 is, in the condition shown in FIG. 1, spaced from the front face 41 of the plunger 18.

Figure 2:
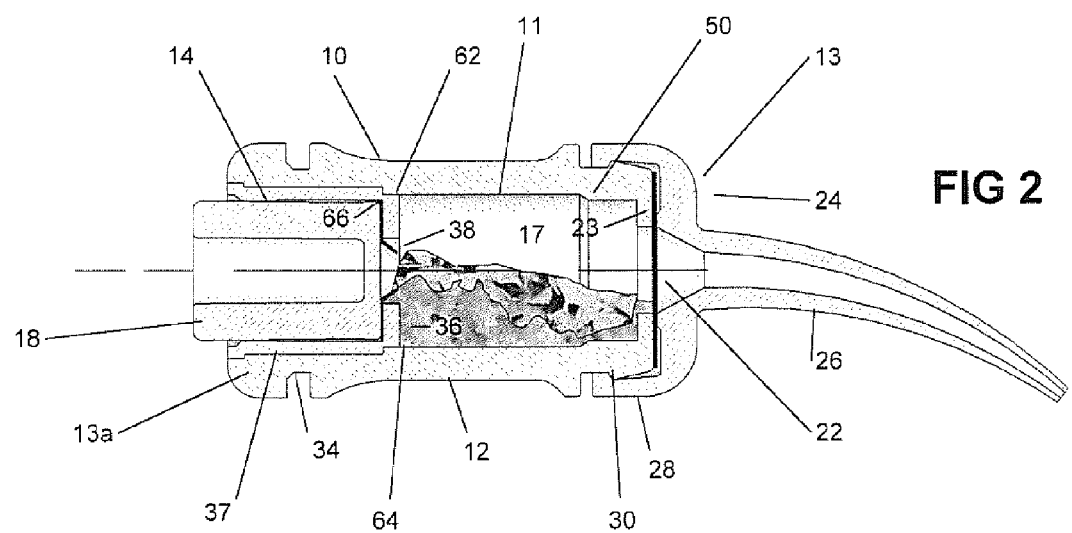
FIG. 2 is a longitudinal sectional view of the container of FIG. 1 in a partially activated condition.

Referring to FIG. 2, there is shown the container 10 in an activated position. The activated position is achieved through the plunger 18 being depressed. This action causes the plunger 18 to be moved so that an inner end thereof contacts the inner wall 36. This displaces the liquid so that the weakened portion 38 of the inner wall 36 breaks due to the hydraulic pressure applied to it by the liquid. The liquid is then forced into the main chamber 17 of the body 12 to contact the powder in the chamber 17. The container 10 may then placed into a known vibrating mixing device. The liquid and the powder are admixed and thereby form a paste in the chamber 17.

Figure 3:
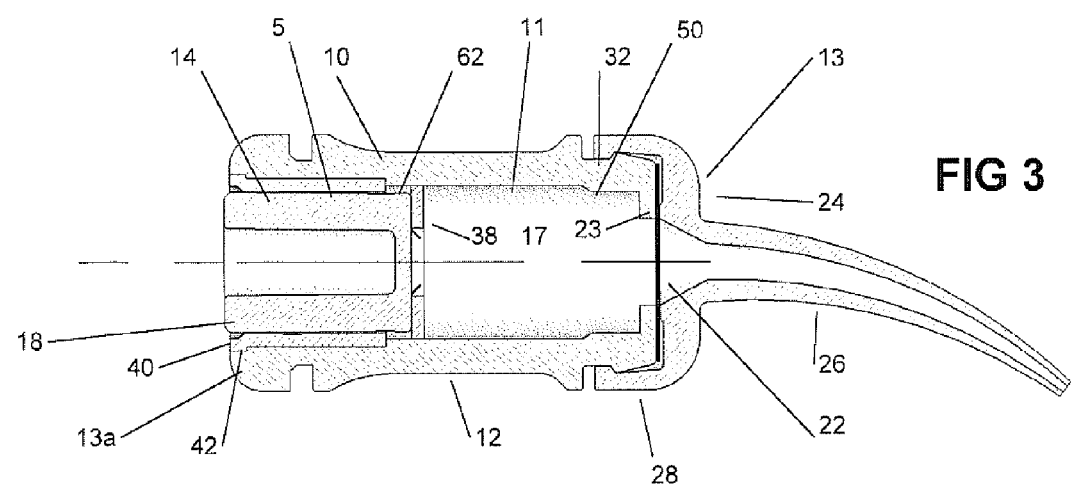
FIG. 3 is a longitudinal sectional view of the container of FIG. 1 in a further partially activated condition.

Referring to FIG. 3, there is shown the container 10 after the plunger 18 has been depressed and the liquid and the powder have been mixed to form a paste. The main chamber 17 of the body 12 now contains the paste. A front part of the liquid receptacle 14 including the inner wall 36 thereof has broken away from the remainder of the liquid receptacle 14. This is caused by force being transferred from the plunger 18 to the front part of the liquid receptacle 14 during dispensing of the paste with a dispensing apparatus. The remainder of the liquid receptacle 14 remains in place by virtue of an outwardly projecting annular step 40 on the liquid receptacle 14 engaging with an annular recess 42 in the inner surface 11 of the body 12 (see FIG. 3).

Figure 4:
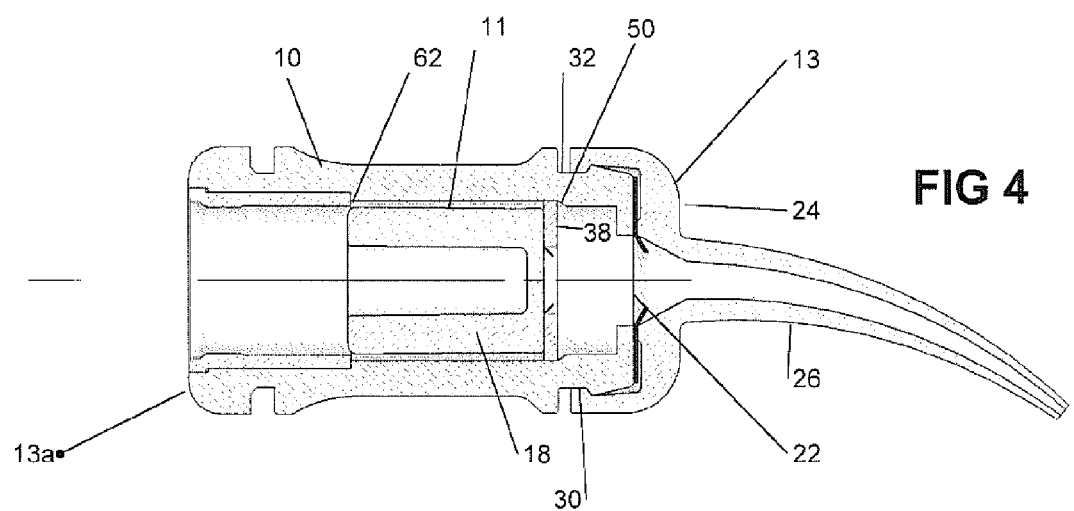
FIG. 4 is a longitudinal sectional view of the container of FIG. 1 in a yet further partially activated condition.
Figure 6:
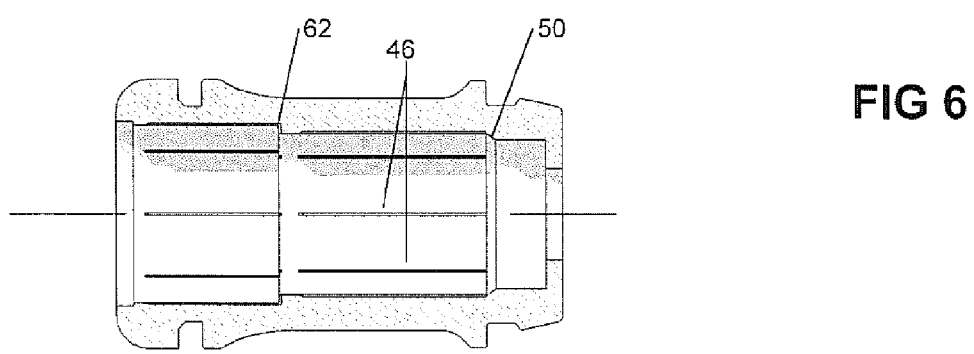
FIG. 6 is a longitudinal section of a body of the container of FIG. 1.
Figure 7:
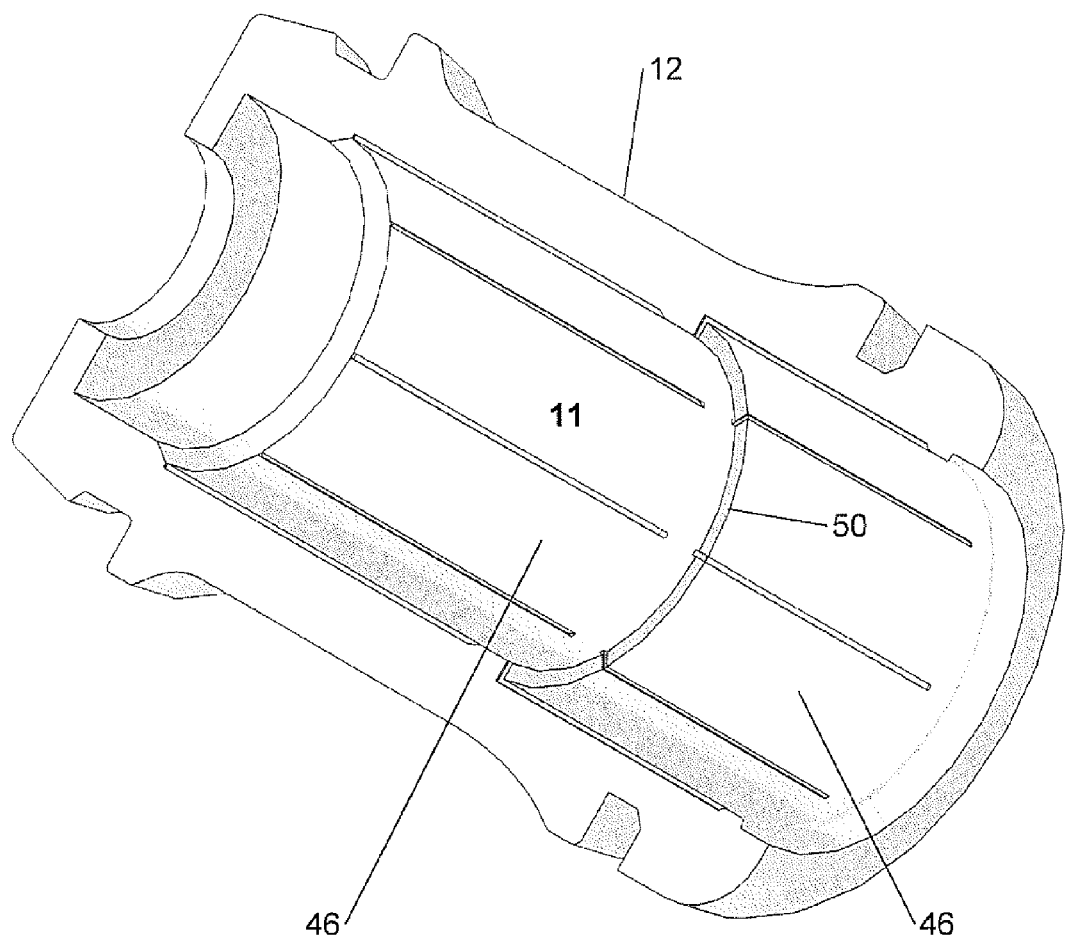
FIG. 7 is a perspective sectional view of the body shown in FIG. 6.

As shown in FIG. 4, the plunger 18 forces the front of the liquid receptacle 14 along the main chamber 17, where the front part of the liquid receptacle 14 acts as a seal and prevents paste from travelling rearwardly. Means such as slots located in the main body internal wall 11 may be provided to act as vent means for entrapped air to escape from the powder. The entrapped air may vent into a recess created from the separation of the front part of the liquid receptacle 14. The slots may take the form of a plurality of elongated substantially parallel slots 46 which can be seen in FIG. 6 or 7, or other forms.

In FIGS. 1 to 5 it can be seen that the internal surface of the container 10 of the body 12 has an internal step 62 such that the proximal end 13a of the body 12 is of larger dimension than the distal end 13.

Further, the side wall 37 of the receptacle is provided with an open sided annular recess 64 adjacent the inner wall 36. The recess 64 engages with the step 62 initially as shown in FIG. 1.

As can be seen the arrangement of the recess 64 and the step 62 enables the receptacle 14 to have a thin section 66 adjacent the inner wall 36. Thus, when force is applied to the plunger 18, as described hereinabove, the inner wall 36 breaks free of the receptacle 14 as shown in FIG. 3 at the thin section 66. This is because the section 66 is relatively weak compared to the inner wall 36. Also, because the distal end 13 of the chamber 17 is smaller in internal diameter than the proximal end portion 13a, all of the force applied to the plunger 18 is concentrated at the step 62 and the thin section 66. Thus, the inner wall 36 breaks away as described above, in use.

Figure 5:
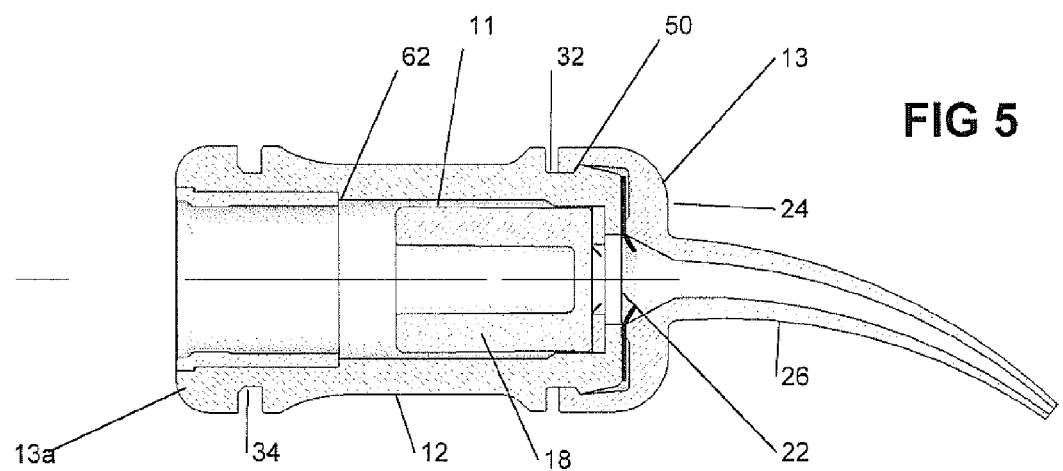
FIG. 5 is a longitudinal sectional view of the container of FIG. 1 in a fully activated condition.

Referring to FIG. 5, there is shown the container 10 once substantially all of the paste has been dispensed. The front part of the liquid receptacle 14 has been displaced forward by the plunger 18 until it approaches the flange 23 of the body 12. As the plunger 18 is displaced forwardly hydraulic pressure on the paste bursts the membrane 22, allowing fluid communication between the main chamber 17 and the nozzle 26 and subsequent dispensing of the paste to the desired location.

It can be seen that the internal surface 11 has a compression zone comprising a stepped region 50 of reduced cross sectional dimension where limited resistance is imparted to movement of the front broken away part of the liquid receptacle 14. It is found that with low viscosity material in particular, the limited resistance imparted by the step 50 reduces the risk of uncontrolled extrusion of the low viscosity material.

The stepped region 50 slows down advancement of the front part of the liquid receptacle and the rate of extrusion of the material is correspondingly slowed down. Preferably, a proximal face of the stepped region 50 is tapered so as to provide a smooth transition from the main part of the internal surface 11 and the stepped region.

In use, a user places the container 10 into an appropriate dispensing device (not shown) by any convenient means 34 to allow for the application of pressure to the plunger 18. Pressure applied to the plunger 18 builds hydraulic pressure against the weakened portion 38 through displacement of the liquid 16. Once the hydraulic pressure reaches a critical point the weakened portion 38 breaks and the liquid 16 then enters the main chamber 17. The plunger 18 is then displaced forward again by the dispensing device. This brings the front face 41 of the plunger 18 into close abutting contact with a rear face of the inner wall 36.

The main chamber 17 now contains the liquid 16 and the powder 20. The user then places the dental applicator in an appropriate mixing device such as a vibration mixer. The agitation caused by the mixing device causes the liquid and the powder to mix and combine to form a paste.

After mixing, further forward displacement of the plunger 18 places increasing pressure against the liquid receptacle 14. Once sufficient force is applied the front section of the liquid receptacle 14 breaks away as shown in FIG. 3. This leaves the side wall 37 of the liquid receptacle 14 substantially intact.

As the plunger 18 is displaced forward slots 46 (see FIGS. 6 and 7) in the interior surface 11 of the main chamber 17 may allow for any air trapped within the container or mixed material to vent into a recess created from the separation of the front part of the liquid receptacle 14 from the side wall 37. Further, it is possible that the mixing process does not fully mix all of the powder components and some residual powder is left behind in, for example, the area between the front part of the liquid receptacle 14 and the internal wall 11 of the body 12. This in practice may cause issues with the area being treated by the dental material becoming contaminated by residual powder component. As the plunger 18 and inner wall 36 move forward the recess is formed behind the inner wall 36. Powder particles that have remained unmixed are able to escape around the front part and into the recess, hence reducing the risk of contamination or exposure of the user of these particles.

Further forward displacement of the plunger 18 will cause the plunger 18 to travel towards the distal end of the body 12 as shown in FIG. 5. This will lead to increased hydraulic pressure against the frangible membrane 22. Once the hydraulic pressure reaches a critical value the membrane 22 will burst. The paste 28 is thus placed in fluid communication with the nozzle 26. Still further, forward displacement of the plunger 18 will cause the paste to travel through the nozzle 26 before finally being dispensed. However, as discussed above, the presence of the step 50 provides a compression zone which imparts a degree of resistance to further movement of the front part of the receptacle 14 from the position shown in FIG. 4 to the position shown in FIG. 5.

Modifications and variations as would be apparent to a skilled addressee are deemed to be within the scope of the present invention.

The invention claimed is:

1. A dental container for mixing and dispensing dental material,
   said container comprising a hollow body having a proximal end portion, a distal end portion and a main chamber for containing dental powder material therein;
   a dispensing nozzle baying an end cap connected thereto, said end cap being attached to said body at said distal end portion;
   a frangible membrane located adjacent said dispensing nozzle and said distal end portion for forming a seal for retaining said powder in said main chamber;
   a liquid receptacle located within said body between said main chamber and said proximal end portion of said body, said liquid receptacle defined by a circumferential wall and an inner transverse end wall, said inner transverse end wall having a weakened portion;
   a plunger at said proximal end of said body sealingly mounted in engagement with said liquid receptacle, said plunger having a planar front face which is projection free, said plunger being movable axially inwardly of said body for creating hydraulic pressure on liquid within said liquid receptacle and causing said weakened portion to break and cause said inner transverse end wall to break away from said circumferential wall so that liquid within said liquid receptacle enters said main chamber and mixes with powder contained therein for forming a paste; said plunger and said broken away inner end wall being further movable toward said distal end whilst said circumferential wall of said liquid receptacle remains stationary at said proximal end portion; the further movement of the plunger and the broken away inner transverse end wall creating hydraulic pressure by acting upon said paste for causing said frangible membrane to burst and allowing said paste to flow outwardly through said dispensing nozzle, and said main chamber having a compression zone comprising a stepped region adjacent said distal end portion of reduced cross-sectional dimension for imparting resistance to movement of the broken away inner transverse end wall adjacent said distal end.

2. A dental container according to claim 1, said end cap having an aperture in alignment with said frangible membrane.

3. A dental container according to claim 1, wherein said liquid receptacle includes an outwardly facing open end and a closed inner end, said plunger being mounted in said Open end of said liquid receptacle.

4. A dental container according to claim 1, wherein said body at said proximal end includes an inwardly facing recess arranged to be engaged with an outwardly facing projection on said liquid receptacle for holding said circumferential wall of said liquid receptacle fixed within said body during movement of said plunger.

5. A dental container according to claim 1, wherein said main chamber includes an annular step internally thereof, said liquid receptacle having an annular recess adjacent said inner transverse end wall to provide said liquid receptacle with a thin section adjacent said inner end wall, said annular recess being in initial engagement with said annular step whereby said inner end wall of said liquid receptacle breaks away from said circumferential wall at said thin section under pressure created by said moving plunger.

\* \* \* \* \*